United States Patent
Bray

(10) Patent No.: US 7,776,074 B2
(45) Date of Patent: Aug. 17, 2010

(54) PROCEDURE FOR ALIGNING AND STABILIZING BONE ELEMENTS

(75) Inventor: Robert S. Bray, Studio City, CA (US)

(73) Assignee: Robert S. Bray, Jr., Studio City, CA (US)

( * ) Notice: Subject to any disclaimer, the term of this patent is extended or adjusted under 35 U.S.C. 154(b) by 813 days.

(21) Appl. No.: 11/147,748

(22) Filed: Jun. 8, 2005

(65) Prior Publication Data

US 2006/0293661 A1    Dec. 28, 2006

(51) Int. Cl.
*A61B 17/56* (2006.01)
*A61B 17/58* (2006.01)

(52) U.S. Cl. ..................... 606/279; 606/86 A

(58) Field of Classification Search ............. 606/59–61, 606/72–73, 86, 99, 105; 623/16.11, 17.11
See application file for complete search history.

(56) References Cited

U.S. PATENT DOCUMENTS

| | | | | |
|---|---|---|---|---|
| 4,066,082 A | * | 1/1978 | Arcan et al. | 606/102 |
| 4,271,836 A | | 6/1981 | Bacal et al. | |
| 4,648,388 A | * | 3/1987 | Steffee | 606/61 |
| 5,020,519 A | * | 6/1991 | Hayes et al. | 606/237 |
| 5,129,900 A | | 7/1992 | Asher et al. | |
| 5,282,862 A | * | 2/1994 | Baker et al. | 606/61 |
| 5,425,773 A | | 6/1995 | Boyd et al. | |
| 5,616,143 A | * | 4/1997 | Schlapfer et al. | 606/86 A |
| 5,704,937 A | * | 1/1998 | Martin | 606/86 A |
| 5,720,751 A | * | 2/1998 | Jackson | 606/86 R |
| 5,814,046 A | * | 9/1998 | Hopf | 606/61 |
| 5,910,141 A | * | 6/1999 | Morrison et al. | 606/86 A |
| 5,984,924 A | | 11/1999 | Asher et al. | |
| 6,083,226 A | | 7/2000 | Fiz | |
| 6,123,707 A | * | 9/2000 | Wagner | 606/86 A |
| 6,176,861 B1 | * | 1/2001 | Bernstein et al. | 606/61 |
| 6,179,838 B1 | * | 1/2001 | Fiz | 606/61 |

(Continued)

OTHER PUBLICATIONS

Michael K. Rosner, M.D., David W. Polly, Jr., M.D., Timothy R. Kuklo, M.D., and Stephen L. Ondra, M.D., "Thoracic Pedicle Screw Fixation for Spinal Deformity", Neurosurg Focus, vol. 14, Jan. 2003, pp. 1-6.
Onelook.com Dictionary Search, definition of the word "measuring" at website address <http://www.onelook.com/?w=measuring&ls=a> date website information obtained: Oct. 12, 2007.*

(Continued)

*Primary Examiner*—Eduardo C Robert
*Assistant Examiner*—Mary Hoffman
(74) *Attorney, Agent, or Firm*—Pearne & Gordon LLP

(57) ABSTRACT

The magnitude of the force that can be created when each of a plurality of bone elements, such as the vertebrae of the human spine, is brought into alignment and stabilized by a corrective appliance comprising bone fasteners, such as pedicle screws attached to the bone elements, and one or more aligning devices, such as fixation rods, is measured and constrained. The force required to bring the bone element into alignment with the aligning device is maintained below a selected magnitude. In some instances, in order to maintain the magnitude of the force below the selected magnitude, it may be necessary to make an adjustment so that the bone fastener can be secured to a respective aligning device without increasing the force to or beyond the selected magnitude.

31 Claims, 4 Drawing Sheets

U.S. PATENT DOCUMENTS

| | | | |
|---|---|---|---|
| 6,616,667 B1 | 9/2003 | Steiger et al. | |
| 6,648,888 B1 * | 11/2003 | Shluzas | 606/86 A |
| 6,726,692 B2 * | 4/2004 | Bette | 606/99 |
| 6,746,449 B2 * | 6/2004 | Jones et al. | 606/86 A |
| 6,821,277 B2 * | 11/2004 | Teitelbaum | 606/61 |
| 7,371,239 B2 * | 5/2008 | Dec et al. | 606/279 |
| 2002/0095153 A1 * | 7/2002 | Jones et al. | 606/61 |
| 2002/0120275 A1 * | 8/2002 | Schmieding et al. | 606/104 |
| 2003/0236529 A1 * | 12/2003 | Shluzas et al. | 606/105 |
| 2005/0059969 A1 * | 3/2005 | McKinley | 606/61 |
| 2007/0276379 A1 * | 11/2007 | Miller et al. | 606/61 |

OTHER PUBLICATIONS

"Pedicle Screws for Spine Fusion", Spine-health.com, www.spine-health.com/topics/surg/overview/lumbar.lumb09_ped.html, 2 pages.

"The Operations, Patient Guide to Pedicle Screw Fixation" Neurosurgery Associates, www.neurosurgery-associates.com/pedicle.htm, 4 pages.

* cited by examiner

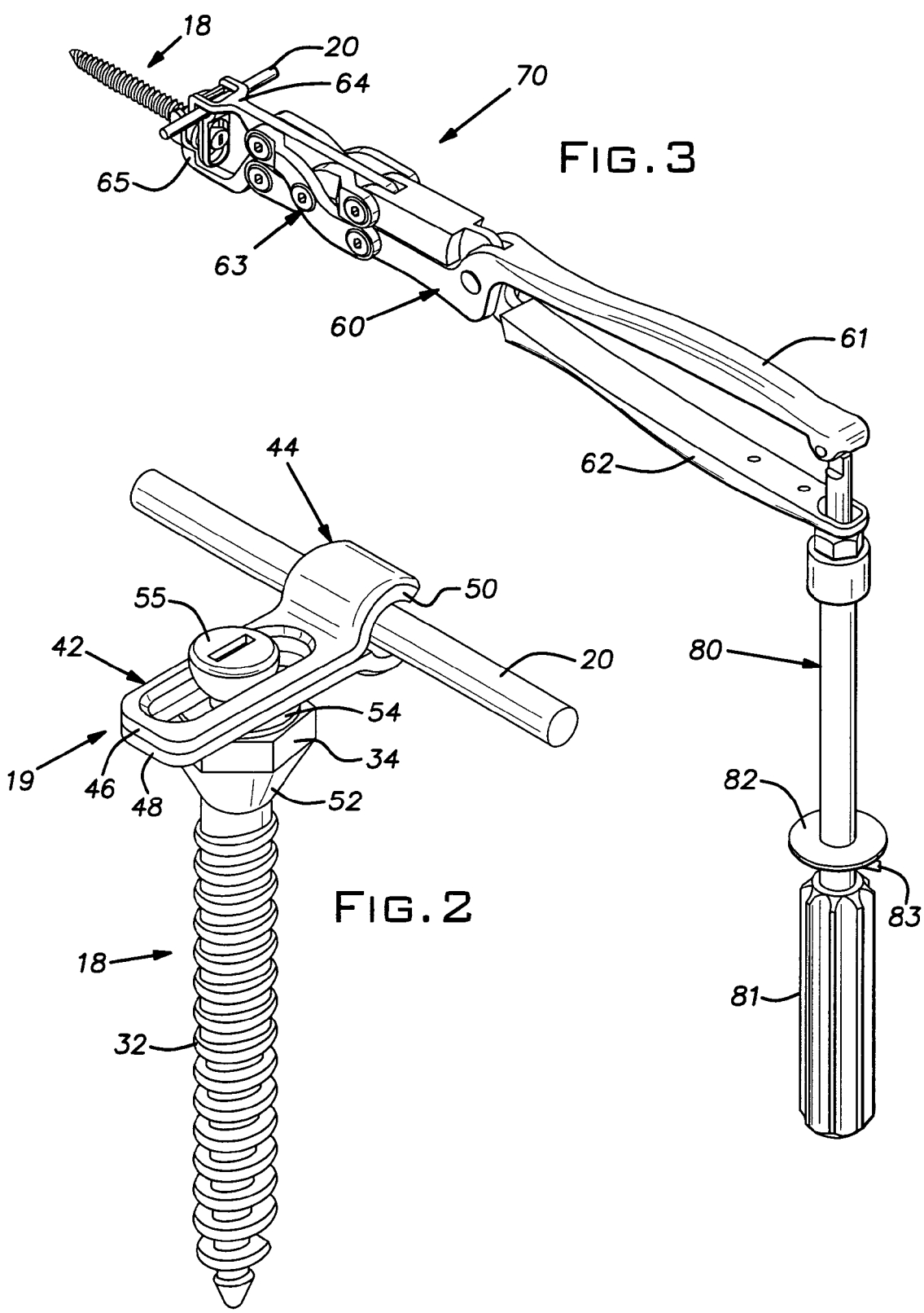

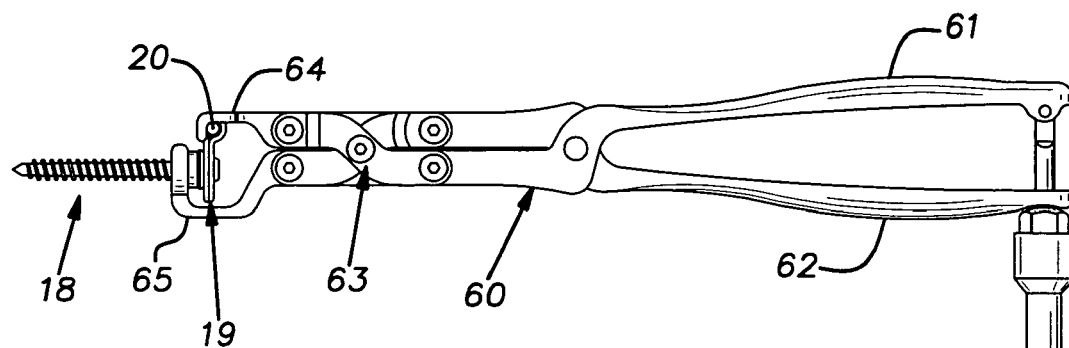
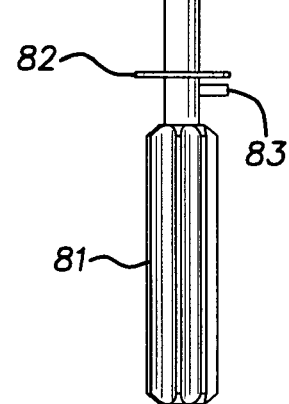
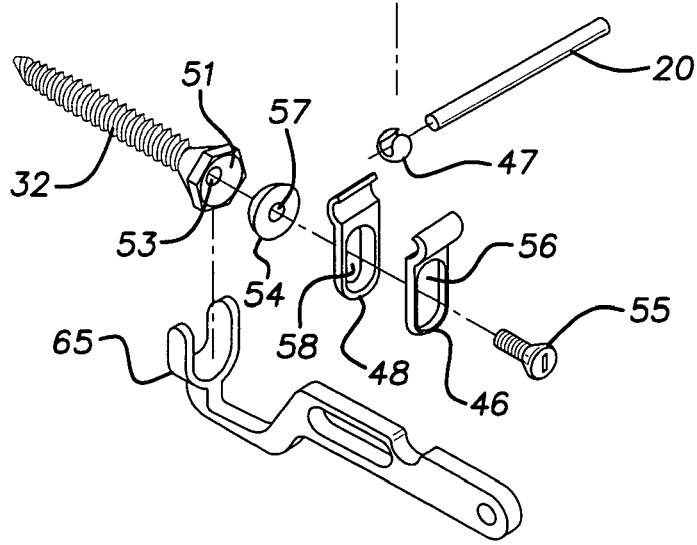
FIG. 5
FIG. 6

PROCEDURE FOR ALIGNING AND STABILIZING BONE ELEMENTS

FIELD OF THE INVENTION

The present invention concerns a method for aligning and stabilizing a plurality of bone elements, such as the vertebrae of a human spinal column, employing a corrective appliance. In particular, the invention is directed to an aligning and stabilizing method wherein the forces, such as stresses and strains, created by the aligning and stabilizing procedure are determined, balanced as desired and the imposition of forces of a magnitude that could result in an unsatisfactory outcome in the procedure, avoided.

BACKGROUND OF THE INVENTION

Examples of the application of a corrective appliance for aligning and stabilizing a plurality of bone elements include procedures for correcting spinal deformities as well as procedures for the long-term biological fusion of adjacent vertebrae. The objective of corrective procedures for spinal deformities is to align and stabilize the vertebrae so as to establish a stable, balanced and pain-free spine that is centered over the pelvis in the coronal and sagittal planes. It is desirable to keep to a minimum the number of vertebrae that are fused in that case so that as much flexibility as possible is retained in the spine. However, there are instances where stabilization of the spine necessarily involves the fusion of vertebrae.

A typical procedure for aligning and stabilizing the human spinal column involves the use of aligning devices such as high-strength metal rods, sometimes referred to as fixation rods, that are secured to bone fasteners that are attached to the vertebrae of the spinal column. The metal rods, in cooperation with the bone fasteners, serve to align and stabilize the vertebrae. Particular bone fasteners that have found acceptance in bone aligning and stabilizing procedures comprise pedicle screws. After access to the vertebrae is gained through an appropriate incision, a first grouping of pedicle screws is attached to one side of respective vertebrae that are to be aligned and stabilized and a second grouping of pedicle screws is attached to the other side of respective vertebrae. The attachments of the pedicle screws to the vertebrae are made at the vertebrae pedicles. The first grouping of pedicle screws is secured to a first fixation rod and the second grouping of pedicle screws is secured to a second fixation rod. The procedure of securing the pedicle screws to the fixation rods tends to move the vertebrae into alignment with the rods and corrects any deformity in the spine.

It will be appreciated that such an aligning procedure, particularly in the case of severe spinal deformities, can create significant forces in the nature of stresses and strains both in the spinal column and in the corrective appliance. It will also be understood that it is possible for these forces to become so great that the aligning procedure does not progress satisfactorily.

SUMMARY OF THE INVENTION

The magnitude of the force that can be created when each of a plurality of bone elements, such as the vertebrae of the human spine, is brought into alignment and stabilized by a corrective appliance comprising bone fasteners, such as pedicle screws attached to the bone elements, and one or more aligning devices, such as fixation rods, is measured, balanced and constrained. The force required to bring the bone element into alignment with an aligning device is maintained below a selected magnitude. In some instances, in order to maintain the magnitude of the force below the selected magnitude, it may be necessary to make an adjustment so that the bone fastener can be secured to a respective aligning device without increasing the force to or beyond the selected magnitude.

According to one aspect, a method of aligning and stabilizing a plurality of bone elements, such as the vertebrae of a human spinal column for example, employs bone fasteners, such as pedicle screws for example, secured to the plurality of bone elements and one or more aligning devices, such as fixation rods for example, for imparting to the bone elements, in cooperation with the bone fasteners, a desired alignment of the bone elements. The method comprises gaining access to the bone elements and attaching respective bone fasteners to the plurality of bone elements. Initially, one or more of the bone fasteners that has been attached to a respective bone element is secured to a respective one of the one or more aligning devices. Thereafter, the following procedure is applied for the purpose of securing to one of the one or more aligning devices selected ones of the remaining bone fasteners that have been attached to the bone elements: an increasing compressive force is applied between the selected bone fastener and a respective one of the one or more aligning devices to which the bone fastener is to be secured so as to incrementally bring the bone element to which the bone fastener is attached nearer into alignment with the respective one aligning device while measuring the magnitude of the increasing compressive force; the application of the increasing compressive force is discontinued prior to the measured magnitude of the increasing compressive force reaching a selected magnitude; and the selected bone fastener is then secured to the respective one aligning device. Any nonselected ones of said other bone fasteners are secured to a respective one of the one or more aligning devices. In a particular aspect, a respective one of the one or more aligning devices is initially secured to two of the bone fasteners that have been attached to respective bone elements.

According to another aspect, following the discontinuation of the application of the increasing compressive force, and prior to securing the selected bone fastener to the respective one aligning device, an adjustment is made to enable the selected bone fastener to be secured to the respective one aligning device without further increasing the compressive force to the selected or a greater magnitude.

According to still another aspect, a respective coupling member is employed to secure each of one or more of the selected bone fasteners to a respective one of the one or more aligning devices. A first portion of each coupling member is secured to the respective selected bone fastener and a second portion of each coupling member is secured to a respective one of the one or more aligning devices. In a particular aspect, the first portion of the coupling member includes a plurality of sites at which the respective selected bone fastener maybe secured and the effective length of the coupling member and the proximity of the second portion of the coupling member to a respective one of the one or more aligning devices thereby adjusted.

In the foregoing cases, any adjustment that is made prior to securing the selected bone fastener to the respective one aligning device comprises one or more of the following manipulations: (a) permanently bending the respective one aligning device to place the respective one aligning device nearer the selected bone fastener; (b) loosening the respective one aligning device from one or more of the bone fasteners to which the respective one aligning device has been previously secured; (c) providing a coupling member of a sufficient length that the first portion of the coupling can be secured to the selected bone fastener and the second portion of the coupling can be secured to the respective one of the aligning devices; and (d) adjusting the effective length of the coupling member by adjusting the site of attachment of the selected bone fastener to the first portion of the coupling member.

With respect to each of the foregoing aspects, a first grouping of pedicle screws can be attached to one side of respective vertebrae at the vertebrae pedicles and secured to a first fixation rod directly or by means of respective coupling members and a second grouping of pedicle screws can be attached to the other side of respective vertebrae at the vertebrae pedicles and secured to a second fixation rod directly or by means of respective coupling members.

BRIEF DESCRIPTION OF THE DRAWINGS

The detailed description of the invention that is set forth below is presented with reference to the accompanying drawings wherein the same reference numerals denote the same elements in the several views and wherein:

FIG. 2 is a perspective view of a pedicle screw of the type employed in the corrective appliance illustrated in FIG. 1 shown attached to a fixation rod by means of a coupling member;

FIG. 3 is a perspective view of a compressor and torque measuring driver that can be employed in the method of the present invention to apply a measured compressive force between a pedicle screw and a fixation rod so as to bring the bone element to which the pedicle screw is attached into alignment with the fixation rod after which the pedicle screw may be secured to the fixation rod by means of the coupling member;

FIG. 5 is a side elevational view of the arrangement of FIG. 3; and

FIG. 6 is an expanded perspective view of the jaws of the compressor of FIG. 3 and the components of the pedicle screw, the coupling member and the fixation rod.

DETAILED DESCRIPTION OF AN EMBODIMENT OF THE INVENTION

The detailed description of the embodiment of the invention that follows makes reference to the application of the invention to the correction of a deformity in the human spinal column such as curvature of the spine. However, based on the detailed description that follows, it will be obvious to those of ordinary skill in the art that the method of the invention can also be used in other circumstances and settings where it is desired to align and stabilize a plurality of bone elements such as, for example, in connection with other types of pathologies affecting the vertebrae of the spine.

Figure 1:
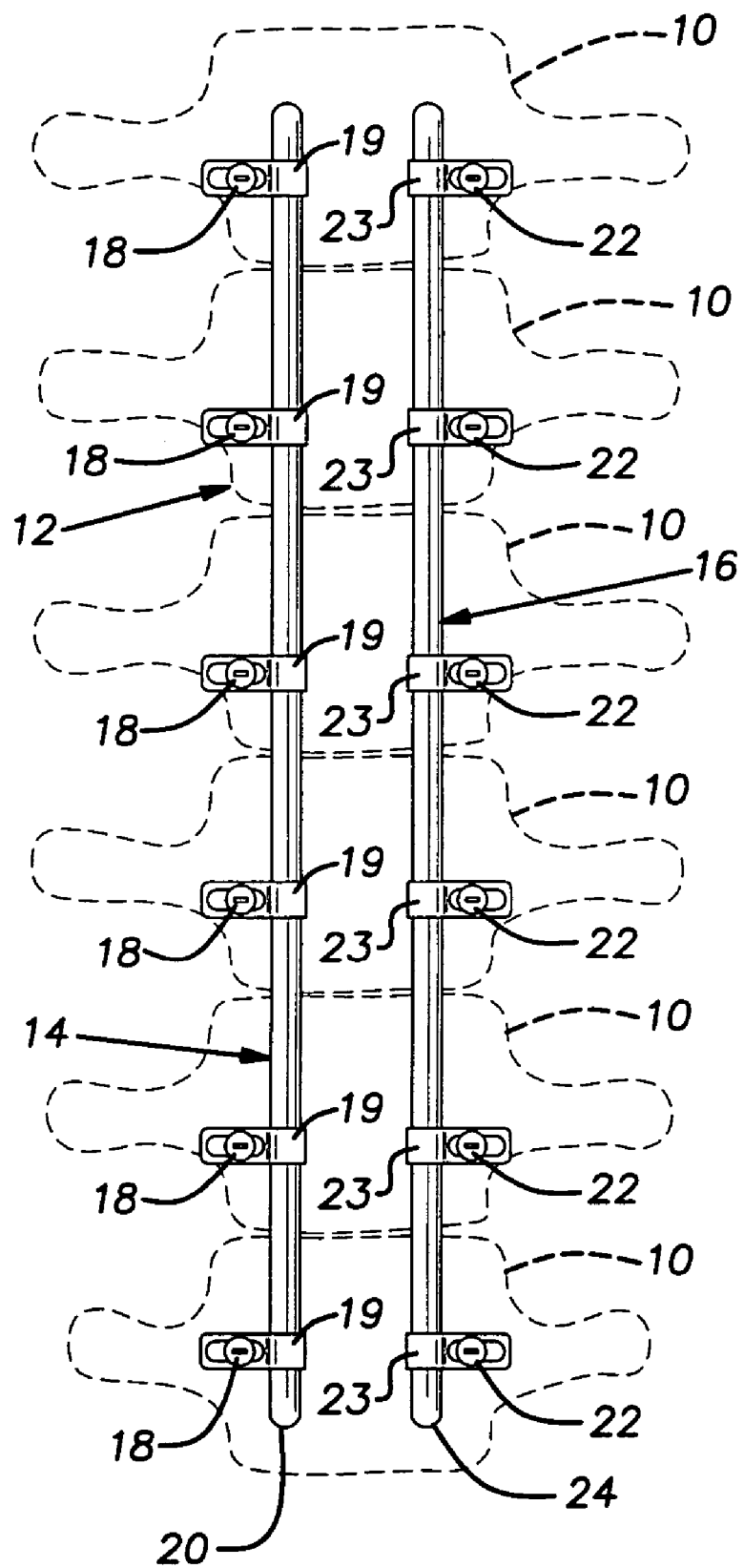
FIG. 1 is an elevated schematic view of a human spinal column that has been aligned and stabilized by the application of a corrective appliance comprising first and second groupings of pedicle screws that are secured to respective fixation rods by means of coupling members.

Referring first to FIG. 1, there is illustrated a plurality of bone elements, in the embodiment of vertebrae 10 of a human spinal column, that have been successfully brought into alignment and stabilized by the application of a corrective appliance or fixation assembly, indicated generally at 12. The corrective appliance 12 is comprised of two fixation units 14 and 16. Each fixation unit comprises an aligning device such as a fixation rod for example and a grouping of bone fasteners that are attached to respective vertebrae. In the embodiment of the invention shown in FIG. 1, the bone fasteners comprise pedicle screws that are attached to respective vertebrae. Specifically, a first grouping of pedicle screws 18 is attached to one side of respective vertebrae at the vertebrae pedicles and the first grouping of pedicle screws is secured to a respective one of one or more aligning devices such as a first fixation rod 20. A second grouping of pedicle screws 22 is attached to the other side of respective vertebrae at the vertebrae pedicles and the second grouping of pedicle screws 22 also is secured to a respective one of one or more aligning devices such as a second fixation rod 24. The fixation rods, typically, are made of a high strength metal such as a stainless steel or a titanium alloy. The pedicle screws 18 are secured to the first fixation rod 20 by means of respective coupling members 19, and the pedicle screws 22 are secured to the second fixation rod 24 by means of respective coupling members 23.

Although the present invention can be employed with aligning devices other than fixation rods, and bone fasteners other than pedicle screws of a particular design, as will be familiar to those having ordinary skill in the art, the corrective appliance shown in the drawings makes use of a type of pedicle screw that is illustrated in FIG. 2 and is described in my copending U.S. patent application Ser. No. 11/011,794. The corrective appliance shown in the drawings also makes use of fixation rods and coupling members as described in patent application Ser. No. 11/011,794 and illustrated in FIG. 2 hereof. Specifically, as shown in FIG. 2, the pedicle screw, indicated generally at 18, includes a shank 32 that has threads for attaching the pedicle screw to the pedicle of a vertebra. Typically, in order to perform the attachment, a hole is drilled in the pedicle of the vertebra, the hole is tapped so as to be provided with threads and the pedicle screw is screwed within the tapped hole, thereby attaching the pedicle screw to the vertebra. The top end 34 of the pedicle screw 18 has a hexagonally shaped circumference so that the screw can be securely grasped by a fastening tool, such as a wrench, and the pedicle screw driven into the tapped hole that has been provided in the pedicle of the vertebra.

As will be familiar to those having ordinary skill in the art, particular designs of pedicle screws are known wherein an aligning device such as a fixation rod can be attached directly to the pedicle screw and such screws can be used with the method of the present invention. However, in the embodiment shown in the drawings, a coupling member, indicated generally at 19 in FIG. 2, is employed to attach each pedicle screw 18 to the fixation rod 20.

Each coupling member 19 has a first portion, indicated generally at 42, that is secured to a respective pedicle screw 18 and a second portion, indicated generally at 44, that is attached to the fixation rod 20. Although coupling members of various constructs can be used to attach the pedicle screws to the fixation rods, in the embodiment illustrated in the drawings, the coupling member 19 includes two substantially identical halves comprising a top half 46 and a bottom half 48. The second portion 44 of each of the top and bottom halves 46 and 48 are inclined away from the first portion 42 of the top and bottom halves, respectively, so as to form a yoke 50. As shown in FIG. 6, grommet 47 is located within the yoke 50, and the fixation rod 20 passes through an opening in the grommet.

Referring once again to the pedicle screw 18 itself, a supporting portion of the pedicle screw, indicated generally at 52, is integral with and is located at the top end of the shank 32. The supporting portion 52 includes a spherical recess 51, as best seen in FIG. 6, in which an adjusting member 54 of the pedicle screw that has a complementary convex spherical surface rests. These complementary spherical surfaces allow for the adjusting member 54 to be universally pivoted within the supporting portion 52 of the pedicle screw, thereby insuring good contact between the adjusting member 54 and the underside of the first portion 42 of the bottom half 48 of the coupling member 19, irrespective of the angularity between the shank 32 of pedicle screw and the coupling member. The supporting portion 52 at the top of the shank 32 of the pedicle screw also includes a threaded cavity 53 for receiving a securing fastener 55 that is provided with complementary threads for securing the securing fastener 55 within the threaded cavity. The adjusting member 54 has an opening 57 that extends through the adjusting member and is in registration with the threaded cavity 53 of the supporting portion 52 of the pedicle screw.

As best seen in FIG. 6, the first portion 42 of the coupling member 19 includes an aperture 56 in the top half 46 of the coupling member and an aperture 58 in the bottom half 48 of the coupling member that enable the coupling member 19 to be secured to the pedicle screw through the instrumentality of the pedicle screw's securing fastener 55. The apertures 56 and 58 are elongated so as to provide a plurality of sites at which the pedicle screw 18 may be secured to the coupling member 19 by the securing fastener 55 and thereby change the effective length of the coupling member and the proximity of the second portion 44 of the coupling member 19 to the fixation rod 20. For example, as illustrated in FIGS. 1 and 2, the pedicle screw 18 is secured to the coupling member 19 at an intermediate site along the first portion 42 of the coupling member. However, if the fixation rod 20 and the pedicle screw 18 were in closer proximity, the pedicle screw would be secured to the first portion 42 of the coupling member 19 nearer the yoke 50 of the coupling member.

From the foregoing description, it will be understood that at such time as it is desired to secure the fixation rod 20 to a respective pedicle screw 18 by means of the coupling member 19, the fixation rod 20 on which the grommet 47 has been placed is disposed within the yoke 50 of the coupling member and the securing fastener 55 is tightened within the threaded cavity 53 of the supporting portion 52 of the pedicle screw 18. This causes the fixation rod 20 to be secured to the second portion 44 of the coupling member 19 and the pedicle screw 18 to be secured to the first portion 42 of the coupling member. The precise manner in which the fixation rod, the pedicle screw and the coupling member are brought together in accordance with the method of the invention so that the fixation rod imparts to the vertebrae, in cooperation with the pedicle screws, a desired alignment of the vertebrae, without applying excessive force is described below.

Although it is not necessary that the fixation units 14 and 16 be identical, the embodiment of the fixation units shown in the drawings each employ pedicle screws and a fixation rod with coupling members joining the pedicle screws to respective fixation rods. Typically, the pedicle screws 18 and 22 are of the same design, the fixation rods 20 and 24 are of the same design and the coupling members 19 and 23 are of the same design. Consequently, the foregoing descriptions of the pedicle screws 18, the fixation rods 20 and the coupling members 19 apply as well to the pedicle screws 22, the fixation rod 24 and the coupling members 23, respectively.

The installation of the fixation units 14 and 16 can be performed in a number of ways. For example, the entire first grouping of pedicle screws 18 and associated coupling members 19 can be installed first, together with the fixation rod 20, and the entire second grouping of pedicle screws 22 and associated coupling members 23, together with the fixation rod 24, installed thereafter. Altenatively, the entire first and second groupings of pedicle screws and associated coupling members may be installed initially and the two fixation rods installed sequentially thereafter. As a further non-limiting example of an installation procedure, one or several of the pedicle screws 18 or 22 may be attached to the vertebrae that lie nearest their final aligned position and a respective fixation rod secured to those pedicle screws before additional pedicle screws are attached to other vertebrae and secured to a respective fixation rod. Whatever the case, it will be understood that because the vertebrae initially are out of alignment, while the fixation rod in the embodiment shown in the drawings, essentially, lies in a straight line, once the initial pedicle screw or pedicle screws that have been attached to respective vertebrae are secured to a respective fixation rod, a compressive force must be applied between the pedicle screws that are attached to the other vertebrae and the fixation rod to move the other vertebrae nearer into alignment with the fixation rod. It will also be understood that as the procedure of securing to the fixation rod additional pedicle screws in successive vertebrae continues, the fixation unit will tend to become more and more rigid and the forces required to move unsecured vertebrae into alignment with the fixation rod can become even greater. During this procedure, it often is the case that the forces required to align the vertebrae with the fixation rods become so great that undesirable stress and strains are experienced.

In order to minimize the likelihood of the imposition of undesirable forces, the present invention provides a procedure for measuring the magnitude of an incrementally increasing compressive force that is applied between a bone fastener that has been attached to a bone element and an aligning device, as the bone fastener and the aligning device are moved toward one another by the incrementally increasing compressive force and the bone element to which the bone fastener is attached comes nearer into alignment with the aligning device. According to the present invention, the incrementally increasing compressive force is continued to be applied until the bone element reaches satisfactory alignment with the aligning device at which point the bone fastener and the aligning device are secured to one another. However, if the magnitude of the incrementally increasing compressive force reaches a selected magnitude that presents a risk of the imposition of an undesirable force, before the bone element attains satisfactory alignment with the aligning device, the practitioner may have no choice but to allow the bone element to remain in a condition of incomplete alignment and make whatever adjustments may be necessary to secure the bone fastener in the bone element to the aligning device. On the other hand, it may be possible in some instances to make an adjustment that lessens the magnitude of the compressive force. In that case, the compressive force can be increased from the reduced magnitude and the bone element brought nearer into alignment with the aligning device. Thereafter, the bone screw can be secured to the aligning device. There are several ways in which adjustments can be made so that the bone fastener and the aligning device can be secured to one another without the compressive force exceeding the selected magnitude, and they are described below.

For applying an incrementally increasing compressive force between a bone fastener and an aligning device, a tool, indicated generally at 70, can be used in accordance with the present invention. The tool 70 and its method of application is best understood with reference to FIGS. 4, 5 and 6. The tool 70 comprises a compressor, indicated generally at 60, and a torque measuring driver, indicated generally at 80, and is of a type that is familiar to those having ordinary skill in the art. From the description that follows, it will be apparent that a tool as shown in the drawings is not the only type of tool that may be used in practicing the invention and other tools familiar to those having ordinary skill in the art and capable of applying a measured compressive force can be employed.

The compressor 60 includes upper and lower handles 61 and 62, respectively. The handles are connected through a series of levers, indicated generally at 63, to an upper jaw 64 and a lower jaw 65. The arrangement of the levers is such that separating or opening the handles 61 and 62 causes the jaws 63 and 64 to separate from one another in a straight line. Alternatively, bringing the handles 61 and 62 together or closing the handles causes the jaws 64 and 65 to move toward one another in a straight line.

The torque measuring driver 80 is used to open and close the handles 61 and 62 and, thereby, the jaws 64 and 65. By grasping the handle 81 of the torque measuring driver 80 and rotating the handle in a counterclockwise direction, the handles 61 and 62 and the jaws 64 and 65 are separated. On the other hand, rotating the handle 81 in a clockwise direction brings the handles 61 and 62 and the jaws 64 and 65 together. A gauge 82 and an indicator 83 are provided on the torque measuring driver for the purpose of providing an indication of the force required to turn the handle 81 of the torque measuring driver and deliver a compressive force to the jaws 64 and 65 against whatever resistance is present between the two jaws. From the foregoing description, it will be understood that if the jaw 64 is placed into engagement with a first element and the jaw 65 is placed into engagement with a second element, the two elements being capable of being brought closer to one another only by the application of a compressive force, the tool 70 provides a means for measuring the force that is applied as the handle 81 is turned and the two elements brought nearer one another.

In accordance with the present invention, at such time as it is desired to apply a compressive force between a bone fastener that has been attached to a bone element and an aligning device for the purpose of bringing the bone element into alignment with the aligning device, while measuring the magnitude of the compressive force, the handle 81 of the torque measuring driver 80 is rotated in a counterclockwise direction so as to open the handles 61 and 62 and the jaws 64 and 65 until the opening between the jaws spans the distance between the bone fastener and the aligning device. At that point, the upper jaw 64 is placed into engagement with the aligning device and the lower jaw 65 is placed into engagement with the bone fastener in a manner so that a compressive force applied to the jaws will cause the bone fastener and the aligning device to come nearer to one another and the bone element to which the bone fastener is attached to come nearer into alignment with the aligning device.

Figure 4:
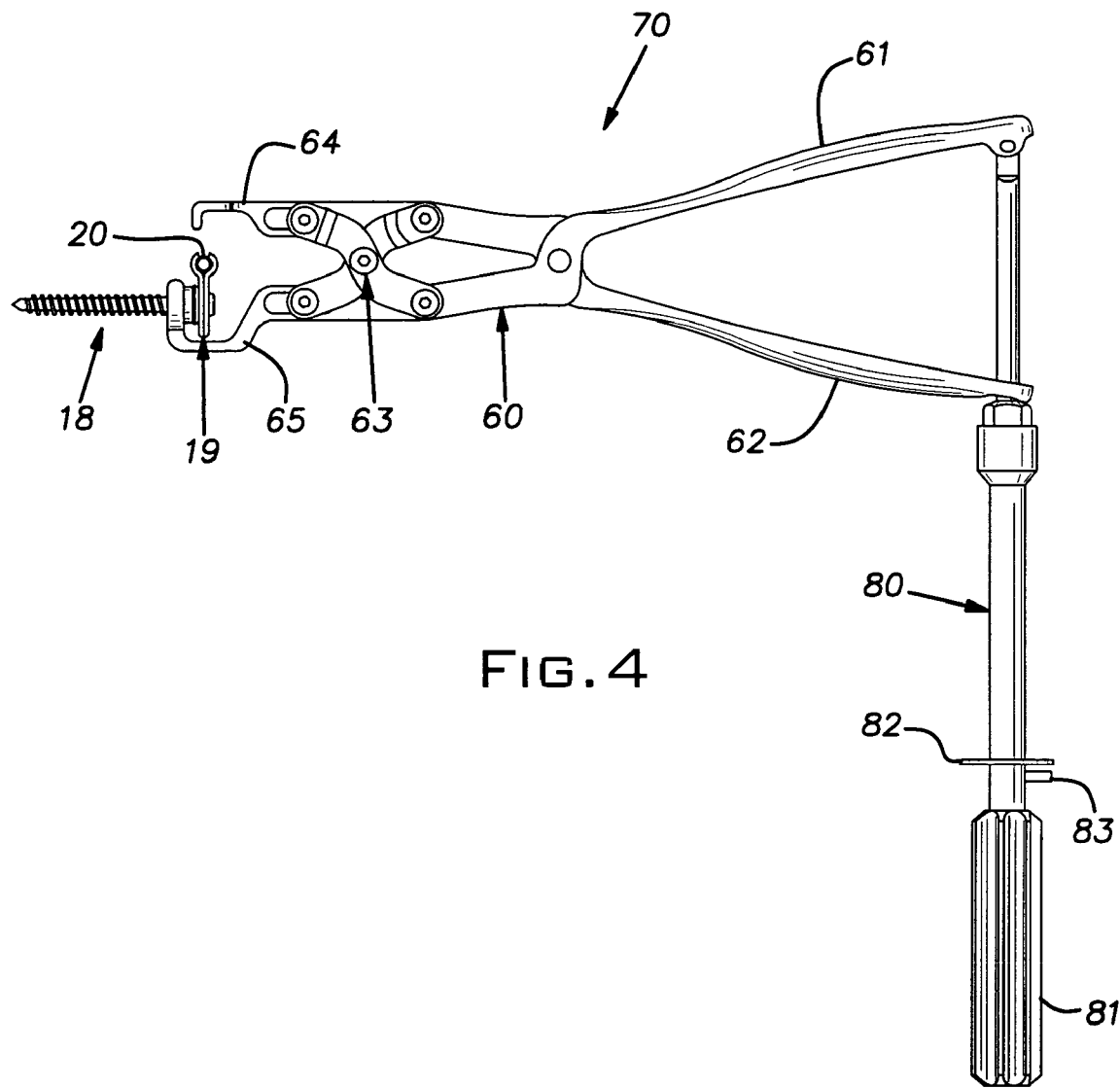
FIG. 4 is a side elevational view of the compressor and torque measuring driver of FIG. 3 with the jaws of the compressor shown in an open position prior to the application of a measured compressive force between the pedicle screw and the fixation rod.

With specific reference to the embodiment illustrated in the drawings, and FIG. 4 in particular, the jaws 64 and 65 are opened so that the upper jaw 64 is positioned over the fixation rod 20 and the lower jaw 65 is placed beneath and into engagement with the supporting portion 52 of the pedicle screw 18. Thereafter, the handle 81 of the torque measuring driver 80 is rotated in a clockwise direction bringing the handles 61 and 62 and the jaws 64 and 65 closer together. While the handle 81 of the torque measuring driver continues to be turned, bringing the handles closer together and the jaws closer together, and incrementally increasing the compressive force applied between the pedicle screw 18 and the fixation rod 20, the practitioner will observe the movement of the indicator 83 along the gauge 82 to determine the magnitude of the compressive force that is being applied. So long as the compressive force does not exceed a selected magnitude, the handle 81 of the torque measuring driver will continue to be turned until the vertebra to which the pedicle screw 18 is attached is brought into alignment with the fixation rod 20, a condition represented by the arrangement shown in FIGS. 3 and 5. On the other hand, if the compressive force indicated by the gauge 82 reaches the selected magnitude before the vertebrae to which the pedicle screw is attached is brought into alignment with the fixation rod 20, the practitioner will cease turning the handle 81 of the torque measuring driver 80 and make whatever adjustment may be required so that the pedicle screw and the fixation rod can be secured to one another without the application between the pedicle screw and the fixation rod of a force of a magnitude exceeding the selected magnitude. It will be appreciated that based on the particular location of a vertebra in the spinal column and other circumstances, the selected magnitude which the compressive force should not attain can vary from vertebra to vertebra.

In a particular application of the present invention, coupling members 19 and 23 of a uniform length are provided in anticipation of the coupling members being of an appropriate length to enable the practitioner to bring all the vertebrae into alignment with the fixation rods 20 and 24 by the application of a force of a magnitude less than a selected magnitude that could impose an unsatisfactory stress or strain, given the allowance that the apertures 56 and 58 in the coupling members provide for adjusting the effective length of the coupling members. In such an application, a coupling member 19, for example, is loosely secured by means of the securing fastener 55 to the pedicle screw and the fixation rod 20. The upper jaw 64 of the tool 70 is then placed into engagement with the fixation rod 20 and the lower jaw 65 of the tool is placed into engagement with the supporting portion 52 of the pedicle screw 18. An incrementally increasing compressive force is then applied by the clockwise rotation of the handle 81 of the torque measuring driver until the vertebra to which the pedicle screw 18 is attached is brought into alignment with the fixation rod 20. The pedicle screw 18 and the fixation rod 20 can then be firmly secured to one another by further tightening of the securing fastener 55 within the threaded cavity 53 in the pedicle screw. It will be appreciated that the elongated nature of the apertures 56 and 58 allow for the movement of the securing fastener 55 within the apertures as the incrementally increasing force is applied thereby providing a plurality of sites at which the pedicle screw may be secured to a first portion of the coupling member and permitting the vertebrae to which the pedicle screw is attached to be placed into alignment with the fixation rod.

If during the procedure described above, while the magnitude of the incrementally increasing compressive force is being measured, the magnitude of the compressive force reaches the selected magnitude before the vertebra to which the pedicle screw 18 is attached comes into the desired alignment with the fixation rod 20, the practitioner will cease turning handle 81 and either tighten the securing fastener 55 to firmly secure the pedicle screw to the fixation rod, notwithstanding the fact that the vertebra has not been brought entirely into alignment, or, by an appropriate manipulation, make an adjustment that will reduce the magnitude of the compressive force without causing the alignment status of the vertebra to deteriorate. The compressive force can then be reapplied and the vertebra brought nearer into alignment with the fixation rod 20 without increasing the compressive force to the selected or a greater magnitude, after which the pedicle screw 18 is firmly secured to the fixation rod 20 by the securing fastener 55. An example of an adjustment that can be made in this regard involves pedicle screws previously secured to the fixation rod. Certain of the previously secured pedicle screws can be loosened and their points of attachment to the fixation rod adjusted by loosening the securing fastener 55, thereby reducing the magnitude of the compressive force applied to the pedicle screw and fixation rod that are being attended to. In this connection, it may be necessary to resecure the securing fasteners that have been loosened only after some adjustment is made to the loosened elements. Other adjustments wherein the magnitude of the compressive force is reduced will be obvious to those having ordinary skill in the art.

The foregoing procedure can also be performed before the coupling member is secured to either the pedicle screw or the fixation rod and is only secured to both after the vertebra to which the pedicle screw is attached is brought into alignment with the fixation rod by the application of a compressive force by the tool 70. The appropriate sized coupling member, with or without elongated apertures, can then be secured to both the pedicle screw and the fixation rod. Of course, in that case, the adjustment that is performed comprises providing an appropriate sized coupling member after the pedicle screw and the fixation rod are in their final positions.

Other applications of the present invention are possible wherein adjustments are made so as to avoid the application of a force between the pedicle screw and the fixation rod of a magnitude that is undesirable. For example, a coupling member with or without elongated slots can be loosely secured to the pedicle screw but not the fixation rod. The tool 70 is employed to apply a compressive force between the pedicle screw and the fixation rod as described above. If the magnitude of the compressive force reaches the selected magnitude but the coupling member is not long enough to enable the fixation rod to be secured to the coupling member, an adjustment is made by substituting a longer coupling member for the one loosely secured to the pedicle screw.

Another manipulation that may be performed for making an adjustment comprises permanently bending the fixation rod in the direction of the pedicle screw to place the fixation rod nearer the pedicle screw. The pedicle screw can then be secured to the fixation rod directly or by means of a coupling member From the foregoing description it will be understood that the present invention provides a method of aligning and stabilizing a plurality of bone elements, such as the vertebrae 10 of a human spinal column for example. The method comprises gaining access to the bone elements, such as through an appropriate incision, and attaching respective bone fasteners, such as the pedicle screws 18, to the plurality of bone elements. Initially, one or more of the bone fasteners that has been attached to a respective bone element is secured to a respective one of one or more aligning devices, such as the fixation rod 20. Thereafter, the following procedure is performed on each of selected ones of the bone fasteners after the selected bone fasteners have been attached to the bone elements: an increasing compressive force is applied to the selected bone fastener and a respective one of the one or more aligning devices to which the bone fastener is to be secured, such as by the use of a tool 70, so as to incrementally bring the bone element to which the bone fastener is attached nearer into alignment with the respective one aligning device while measuring the magnitude of the increasing compressive force, such as by means of the indicator 82 and the indicator gauge 83 of the tool 70; the application of the increasing compressive force is discontinued prior to the measured magnitude of the increasing compressive force reaching a selected magnitude; and the selected bone fastener is then secured to the respective one aligning device. Any nonselected ones of the said other bone fasteners are secured to a respective one of the one or more aligning device. In a particular aspect, a respective one of the one or more aligning devices is initially secured to two of the bone fasteners that have been attached to respective bone elements.

In certain cases, following the discontinuation of the application of the increasing compressive force, and prior to securing the selected bone fastener to the respective one aligning device, an adjustment is made to enable the selected bone fastener to be secured to the respective one aligning device without further increasing the compressive force to the selected or a greater magnitude.

A respective coupling member, such as coupling member 19, can be employed to secure each of one or more of the selected bone fasteners to a respective one of the one or more aligning devices. A first portion 42 of each coupling member is secured to a respective bone fastener and a second portion 44 of each coupling member is secured to a respective one of the one or more aligning devices. The first portion of each coupling member can include a plurality of sites at which a respective selected bone fastener may be secured and the effective length of the coupling member and the proximity of the second portion of the coupling member to a respective one of the one or more aligning devices thereby adjusted. The aforesaid adjustments can comprise one or more of the following manipulations: (a) permanently bending the respective one aligning device to place the respective one aligning device nearer the bone fastener; (b) loosening the respective one aligning device from one or more of the other bone fasteners to which the respective one aligning device has been secured; (c) providing a coupling member of a sufficient length that the first portion of the coupling can be secured to the selected bone fastener and the second portion of the coupling can be secured to the respective one of the aligning devices; and (d) adjusting the effective length of the coupling member by adjusting the site of attachment of the selected bone fastener to the first portion of the coupling member.

With respect to the foregoing methods, a first grouping of pedicle screws 18 is be attached to the pedicles on one side of respective vertebrae 10 and is secured to a first fixation rod 20 by means of respective coupling members 19 and a second grouping of pedicle screws 22 is attached to the pedicles on the other side of respective vertebrae 10 and is secured to a second fixation rod 24 by means of respective coupling members 23.

The foregoing description and discussion of the invention has been presented for purposes of illustration and to facilitate the presentation of particular aspects of the invention. The foregoing is not intended to limit the invention to those aspects however. Additionally, although the description of the invention has included discussions of certain variations and modifications, other variations and modifications may become apparent to those of ordinary skill in the art and it is intended that the scope of the invention as set forth in the claims below be inclusive of such variations and modifications.

What is claimed is:

1. A method of aligning and stabilizing a plurality of bone elements comprising:

gaining access to the bone elements;

attaching respective bone fasteners to the plurality of bone elements;

initially securing to a respective one of one or more aligning devices one or more of the bone fasteners that has been attached to a respective bone elements;

thereafter, for each of selected ones of the other bone fasteners after the selected bone fastener has been attached to a respective bone element, (a) applying an increasing compressive force between the selected bone fastener and a respective one of the one or more aligning devices to which the selected bone fastener is to be secured with a tool engaged with the selected bone fastener and a respective one of the one or more aligning devices to which the selected bone fastener is secured to so as to incrementally bring the bone element to which the selected bone fastener is attached nearer into alignment with the respective one aligning device while measuring the magnitude of the increasing compressive force, (b) discontinuing the application of the increasing compressive force prior to the measured magnitude of the increasing compressive force reaching a selected magnitude, and (c) securing the selected bone fastener to the respective one aligning device; and securing to a respective one of the one or more aligning devices any non-selected ones of said other bone fasteners, separate from the step of applying an increasing compressive force, wherein a respective coupling member is employed to secure each of one or more of the selected bone fasteners to a respective one of the one or more aligning devices, a first portion of each coupling member being secured to a respective selected bone fastener and a second portion of each coupling member being secured to a respective one of the one or more aligning devices, and the first portion of each coupling member includes a plurality of sites at which a respective selected bone fastener may be secured and the effective length of the coupling member and the proximity of the second portion of the coupling member to a respective one of the one or more aligning devices thereby adjusted.

2. The method of claim 1 wherein the bone elements comprise vertebrae of a mammalian spinal column.

3. The method of claim 1 wherein the bone elements comprise vertebrae of a human spinal column, the bone fasteners comprise pedicle screws and the aligning devices comprise fixation rods.

4. The method of claim 3 wherein a first grouping of pedicle screws is attached to pedicles on one side of respective vertebrae and is secured to a first fixation rod and a second grouping of pedicle screws is attached to pedicles on the other side of respective vertebrae and is secured to a second fixation rod.

5. The method of claim 4 wherein each fixation rod is initially secured to a respective two of the pedicle screws that have been attached to respective vertebrae.

6. A method of aligning and stabilizing a plurality of bone elements comprising:

gaining access to the bone elements;

attaching respective bone fasteners to the plurality of bone elements;

initially securing to a respective one of one or more aligning devices one or more of the bone fasteners that has been attached to a respective bone elements;

thereafter, for each of selected ones of the other bone fasteners after the selected bone fastener has been attached to a respective bone element, (a) applying an increasing compressive force between the selected bone fastener and a respective one of the one or more aligning devices to which the selected bone fastener is to be secured with a tool engaged with the selected bone fastener and a respective one of the one or more aligning devices to which the selected bone fastener is secured to so as to incrementally bring the bone element to which the selected bone fastener is attached nearer into alignment with the respective one aligning device while measuring the magnitude of the increasing compressive force, (b) discontinuing the application of the increasing compressive force prior to the measured magnitude of the increasing compressive force reaching a selected magnitude, and (c) securing the selected bone fastener to the respective one aligning device; and securing to a respective one of the one or more aligning devices any non-selected ones of said other bone fasteners, separate from the step of applying an increasing compressive force, wherein following the discontinuation of the application of the increasing compressive force, and prior to securing the selected bone fastener to the respective one aligning device, making an adjustment to enable the selected bone fastener to be secured to the respective one aligning device without further increasing the compressive force to the selected or a greater magnitude.

7. The method of claim 6 wherein the bone elements comprise vertebrae of a mammalian spinal column.

8. The method of claim 6 wherein the bone elements comprise vertebrae of a human spinal column, the bone fasteners comprise pedicle screws and the aligning devices comprise fixation rods.

9. The method of claim 8 wherein a first grouping of pedicle screws is attached to pedicles on one side of respective vertebrae and is secured to a first fixation rod and a second grouping of pedicle screws is attached to pedicles on the other side of respective vertebrae and is secured to a second fixation rod.

10. The method of claim 9 wherein each fixation rod is initially secured to a respective two of the pedicle screws that have been attached to respective vertebrae.

11. The method of claim 6 wherein the adjustment comprises one or both of the following manipulations:(a) permanently bending the respective one aligning device to place the respective one aligning device nearer the selected bone fastener; (b) loosening the respective one aligning device from one or more of the bone fasteners to which the respective one aligning device has been previously secured.

12. The method of claim 11 wherein the bone elements comprise vertebrae of a mammalian spinal column.

13. The method of claim 11 wherein the bone elements comprise vertebrae of a human spinal column, the bone fasteners comprise pedicle screws and the aligning devices comprise fixation rods.

14. The method of claim 13 wherein a first grouping of pedicle screws is attached to the pedicles on one side of respective vertebrae and is secured to a first fixation rod and a second grouping of pedicle screws is attached to pedicles on the other side of respective vertebrae and is secured to a second fixation rod.

15. The method of claim 14 wherein each fixation rod is initially secured to a respective two of the pedicle screws that have been attached to respective vertebrae.

16. The method of claim 6 wherein a respective coupling member is employed to secure each of one or more of the selected bone fasteners to a respective one of the one or more aligning devices, a first portion of each coupling member being secured to a respective selected bone fastener and a second portion of each coupling member being secured to a respective one of the one or more aligning devices.

17. The method of claim 16 wherein the bone elements comprise vertebrae of a mammalian spinal column.

18. The method of claim 16 wherein the bone elements comprise vertebrae of a human spinal column, the bone fasteners comprise pedicle screws and the aligning devices comprise fixation rods.

19. The method of claim 18 wherein a first grouping of pedicle screws is attached to the pedicles on one side of respective vertebrae and is secured to a first fixation rod by means of a respective coupling member and a second grouping of pedicle screws is attached to pedicles on the other side of respective vertebrae and is secured to a second fixation rod by means of a respective coupling member.

20. The method of claim 19 wherein each fixation rod is initially secured to a respective two of the pedicle screws that have been attached to respective vertebrae.

21. The method of claim 16 wherein the first portion of each coupling member includes a plurality of sites at which a respective selected bone fastener may be secured and the effective length of the coupling member and the proximity of the second portion of the coupling member to a respective one of the one or more aligning devices thereby adjusted.

22. The method of claim 21 wherein the bone elements comprise vertebrae of a human spinal column, the bone fasteners comprise pedicle screws and the aligning devices comprise fixation rods.

23. The method of claim 22 wherein a first grouping of pedicle screws is attached to pedicles on one side of respective vertebrae and is secured to a first fixation rod by means of respective coupling members and a second grouping of pedicle screws is attached to pedicles on the other side of respective vertebrae and is secured to a second fixation rod by means of respective coupling members.

24. The method of claim 23 wherein each fixation rod is initially secured to a respective two of the pedicle screws that have been attached to respective vertebrae.

25. The method of claim 21 wherein the adjustment comprises one or more of the following manipulations: (a) permanently bending the respective one aligning device to place the respective one aligning device nearer the selected bone fastener; (b) loosening the respective one aligning device from one or more of the other bone fasteners to which the respective one aligning device has been previously secured; (c) providing a coupling member of a sufficient length that the first portion of the coupling member can be secured to the selected bone fastener and the second portion of the coupling can be secured to the respective one of the aligning devices; and (d) adjusting the effective length of the coupling member by adjusting the site of attachment of the selected bone fastener to the first portion of the coupling member.

26. The method of claim 25 wherein the bone elements comprise vertebrae of a human spinal column, the bone fasteners comprise pedicle screws and the aligning devices comprise fixation rods.

27. The method of claim 26 wherein a first grouping of pedicle screws is attached to pedicles on one side of respective vertebrae and is secured to a first fixation rod by means of respective coupling members and a second grouping of pedicle screws is attached to pedicles on the other side of respective vertebrae and is secured to a second fixation rod by means of respective coupling members.

28. The method of claim 1 wherein the step of applying an increasing compressive force while measuring the magnitude of the increasing compressive force includes measuring the magnitude of the increasing force via a portion of the tool.

29. A method of aligning and stabilizing a plurality of bone elements comprising:
    gaining access to the bone elements;
    attaching respective bone fasteners to the plurality of bone elements;
    initially securing to a respective one of one or more aligning devices one or more of the bone fasteners that has been attached to a respective bone elements;
    thereafter, for each of selected ones of the other bone fasteners after the selected bone fastener has been attached to a respective bone element,
    (a) applying an increasing compressive force between the selected bone fastener and a respective one of the one or more aligning devices to which the selected bone fastener is to be secured with a tool engaged with the selected bone fastener and a respective one of the one or more aligning devices to which the selected bone fastener is secured to so as to incrementally bring the bone element to which the selected bone fastener is attached nearer into alignment with the respective one aligning device while measuring the magnitude of the increasing compressive force,
    (b) discontinuing the application of the increasing compressive force prior to the measured magnitude of the increasing compressive force reaching a selected magnitude, and
    (c) securing the selected bone fastener to the respective one aligning device; and
    securing to a respective one of the one or more aligning devices any non-selected ones of said other bone fasteners, separate from the step of applying an increasing compressive force,
    wherein the step of applying an increasing compressive force while measuring the magnitude of the increasing compressive force includes turning a handle of the tool and the step of measuring the magnitude of the increasing force via a portion of the tool includes moving an indicator on the tool to indicate the force required to turn the handle.

30. The method of claim 1 wherein the step of applying an increasing compressive force includes applying force via two jaws of the tool urging the selected bone fastener and the respective one of the one or more aligning devices toward each other.

31. The method of claim 30 wherein the step of applying an increasing compressive force includes using the tool with two movable handles, a compressor attached to the two handles, and the compressor attached to the two jaws.

* * * * *